US00PP26031P3

(12) United States Plant Patent
Hancock

(10) Patent No.: US PP26,031 P3
(45) Date of Patent: Nov. 3, 2015

(54) BLUEBERRY PLANT DENOMINATED 'OSORNO'

(50) Latin Name: *Vaccinium corymbosum*
Varietal Denomination: Osorno

(71) Applicant: Board of Trustees of Michigan State University, East Lansing, MI (US)

(72) Inventor: James F. Hancock, East Lansing, MI (US)

(73) Assignee: Board of Trustees Michigan State University, East Lansing, MI (US)

( * ) Notice: Subject to any disclaimer, the term of this patent is extended or adjusted under 35 U.S.C. 154(b) by 82 days.

(21) Appl. No.: 13/998,457

(22) Filed: Nov. 1, 2013

(65) Prior Publication Data

US 2015/0128313 P1 May 7, 2015

(51) Int. Cl.
*A01H 5/08* (2006.01)

(52) U.S. Cl.
USPC ..... Plt./157

(58) Field of Classification Search
USPC ..... Plt./157
CPC ..... A01H 5/08
See application file for complete search history.

*Primary Examiner* — Kent L Bell
(74) *Attorney, Agent, or Firm* — Cochran Freund & Young, LLC

(57) ABSTRACT

'Osorno' is a new blueberry cultivar of primarily *Vaccinium corymbosum*. The rest of its parentage is from *V. darrowii* (13.3%), *V. angustifolium* (3.8%), *V. tenellum* (<1%), and *V. ashei* (<1%). It is a highly productive cultivar with exceptional fresh fruit quality. It is likely best adapted to the northern highbush production areas where winters are not severe, such as central Chile and the Pacific Northwest, but it is recommended for further trial in colder production regions such as Michigan. Plants of 'Osorno' are vigorous and upright, although the canes can be lax when loaded with fruit. Canes are numerous, moderately branched and the fruit are well exposed. Its berries are large, have small, dry picking scars, light blue color, and excellent firmness and flavor. Its fruit held up extremely well in the unseasonably hot summer of 2012, when temperatures routinely exceeded 30 C.

5 Drawing Sheets

Latin name and variety denomination: The present disclosure relates to a new and distinct variety of *Vaccinium corymbosum*, which is hereby denominated 'Osorno.'

SUMMARY

The present disclosure relates to a new and distinct variety of highbush blueberry plant, denominated 'Osorno.' 'Osorno' is primarily *Vaccinium corymbosum* with 13.3% of its genes coming from *V. darrowii,* 3.8% from *V. angustifolium*, and <1% from *V. tenellum* and *V. ashei*. It is a highly productive cultivar with exceptional fresh fruit quality. It is likely best adapted to the northern highbush production areas where winters are not severe, such as central Chile and the Pacific Northwest, but may be suitable for colder production regions such as Michigan. Plants of 'Osorno' are vigorous and upright, although the canes can be lax when loaded with fruit. Canes are numerous, moderately branched and the fruit are well exposed. Its berries are large, have small, dry picking scars, light blue color, and excellent firmness and flavor. Its fruit holds up extremely well, including in hot summers such as the unseasonably hot summer of 2012 in Michigan and Oregon, when temperatures routinely exceeded 30° C.

BRIEF DESCRIPTION OF THE DRAWINGS

The present variety will become more fully understood from the detailed description and the accompanying drawings, wherein.

DETAILED BOTANICAL DESCRIPTION

The following is a detailed botanical description of the new and distinct variety of blueberry denominated 'Osorno,' its flowers, fruit, and foliage.

Figure 1:
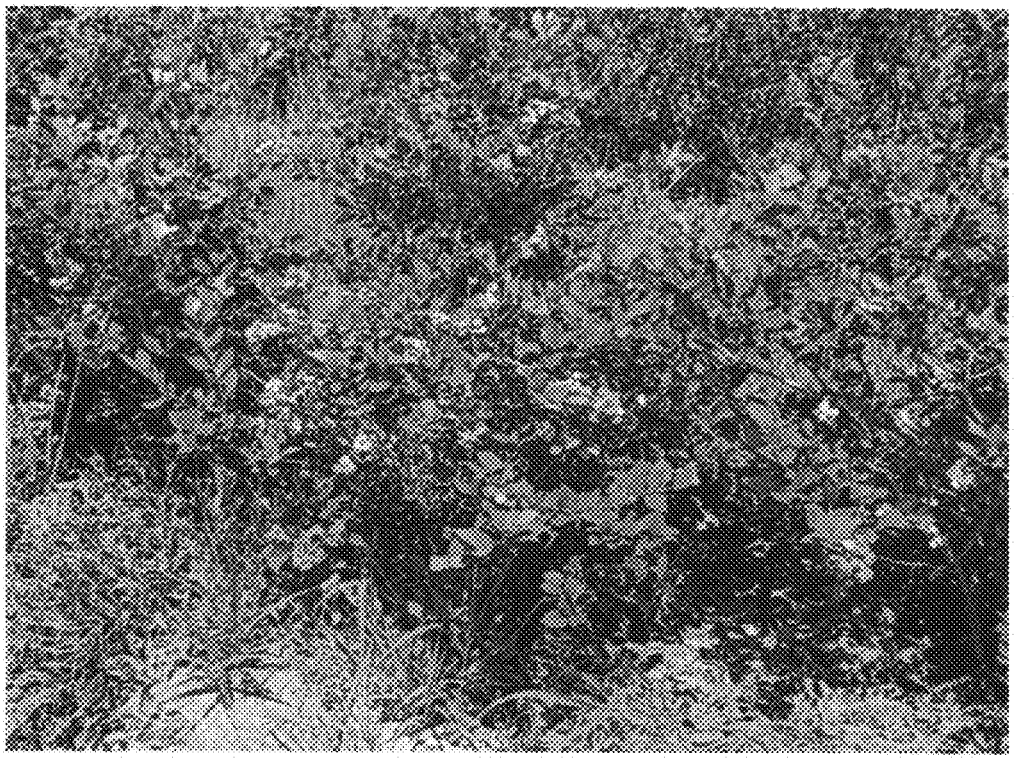
FIG. 1 is a photographic print in full color of a first perspective of a 'Osorno' blueberry bush, wherein the bush is in the foreground and the additional plants or portions thereof in the background and the grass on the ground are not part of the 'Osorno' blueberry blush.
Figure 2:
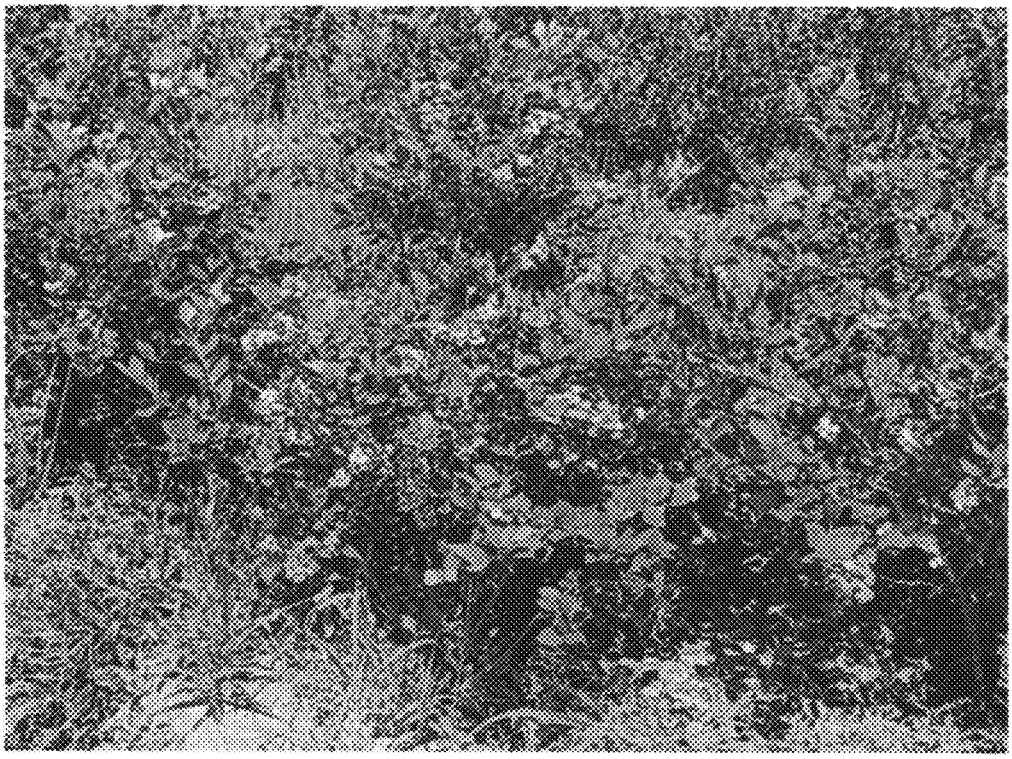
FIG. 2 is a photographic print in full color of a second perspective of a 'Osorno' blueberry bush, wherein the bush is in the foreground and the additional plants or portions thereof in the background and the grass on the ground are not part of the 'Osorno' blueberry blush.
Figure 3:
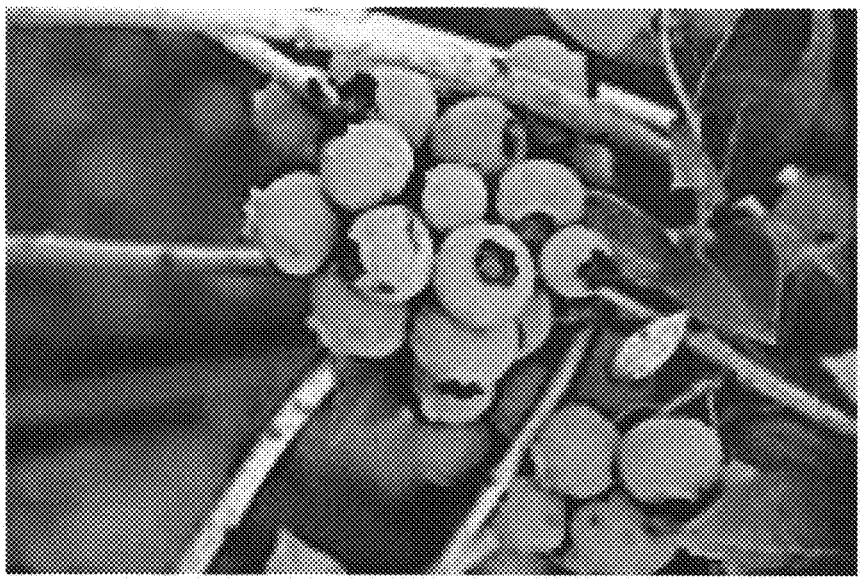
FIG. 3 is a photographic print in full color illustrating a first 'Osorno' branch with exemplary fruit clusters, wherein the fruit shown are mature.
Figure 4:
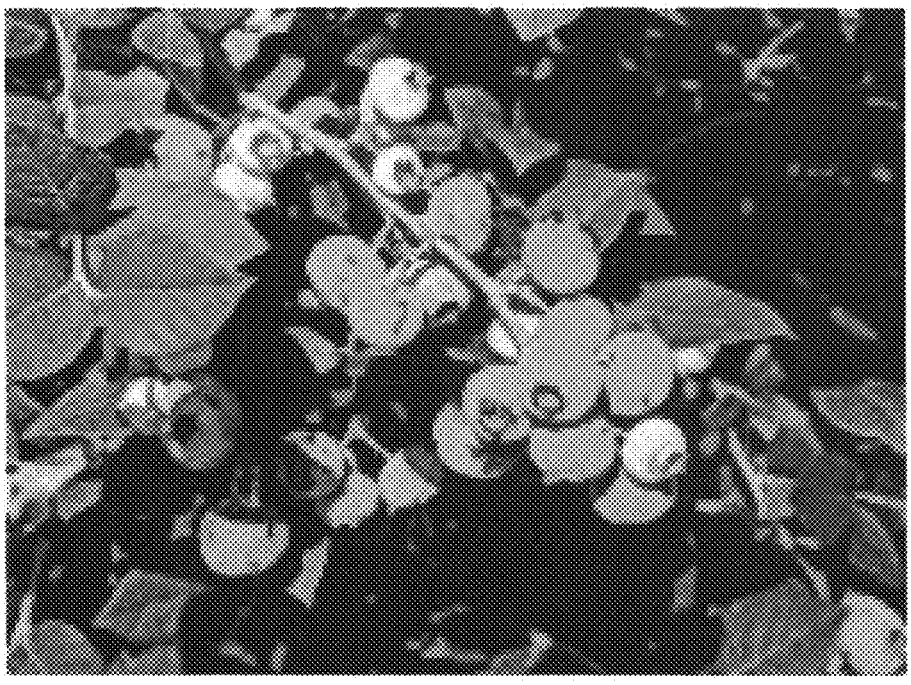
FIG. 4 is a photographic print in full color illustrating a second 'Osorno' branch with exemplary fruit clusters; wherein most, but not all, of the fruit shown are mature.
Figure 5:
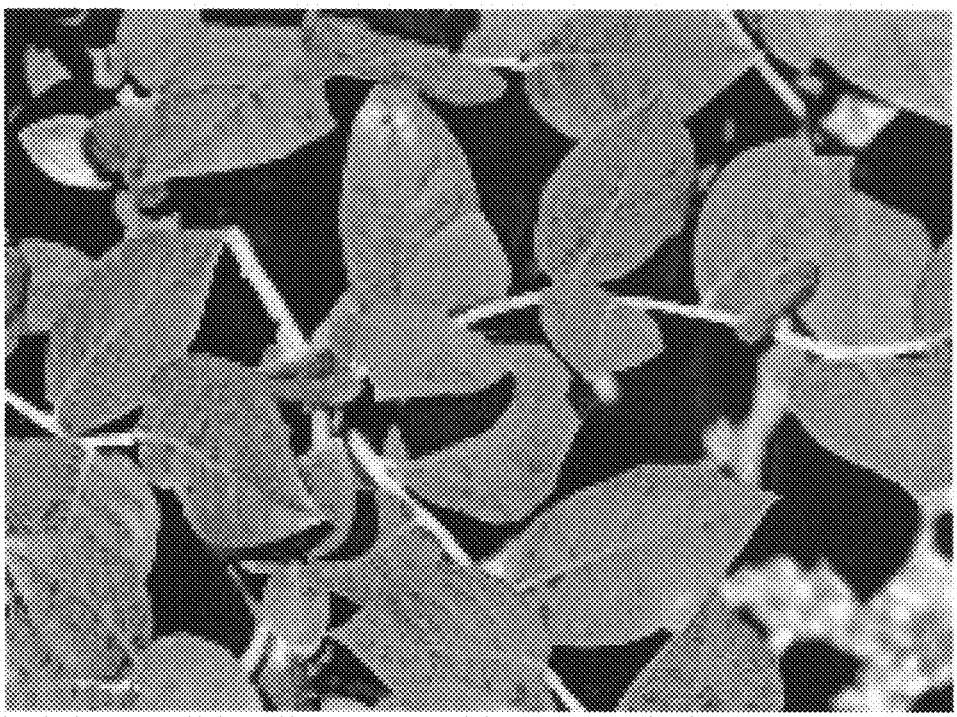
FIG. 5 is a photographic print in full color illustrating an 'Osorno' branch with exemplary leaves.

'Osorno' is primarily *Vaccinium corymbosum* with 13.3% of its genes coming from *V. darrowii,* 3.8% from *V. angustifolium*, and <1% from *V. tenellum* and *V. ashei*. Emasculated flowers of 'Draper,' the female parent (i.e., the seed parent), were pollinated in 2002 with pollen from 'Legacy'. The seeds were germinated, grown in a greenhouse for 1 year and then field planted in Benton Harbor, Mich. 'Osorno' was first selected from a group of 103 siblings in 2006. The selected 'Osorno' plant was first asexually reproduced by cuttings taken from Benton Harbor, Mich. and rooted in East Lansing, Mich. FIG. 1 and FIG. 2 show exemplary 'Osorno' bushes, FIG. 3 and FIG. 4 show 'Osorno' branches with exemplary fruit clusters, and FIG. 5 shows exemplary leaves from an 'Osorno' bush.

The original selection of 'Osorno' was evaluated at Benton Harbor, Mich. from 2003-2007. Softwood cuttings were also set in advanced trials at Grand Junction, Mich., South Haven, Mich., Silverton, Oreg., Lowell, Oreg. and Osorno, Chile. Two year old plants were set at 4×10 foot spacing in 2008 in Michigan, and in 2009 in Oregon and Chile. As discussed further below, the plantings in Michigan were evaluated for three years, and those in Oregon and Chile for two years.

'Osorno' may be propagated by hardwood cuttings in a greenhouse and then planted in the field. Initiation of root development from hardwood cuttings may take about four to six weeks.

Initiation of root development from microshoots takes about three to four weeks. Such methods are discussed in the following references, incorporated by reference herein: Doran, W. L. and Bailey, J. S. "Propagation of the high bush blueberry by softwood cuttings," Bulletin Massachusetts Agricultural Experiment Station; no. 410. Amherst, Mass. Massachusetts State College, 1943; Doehlert, C. A. "Propagating blueberries from hardwood cuttings," Circular (New Jersey Agricultural Experiment Station) 490. New Brunswick, N.J. New Jersey Agricultural Experiment Station, 1945; Doehlert, C. A. "Propagating blueberries from hardwood cuttings," Circular (New Jersey Agricultural Experiment Station) 551. New Brunswick, N.J.: New Jersey Agricultural Experiment Station, 1953; Zimmerman, R. H. 1991. Micropropagation of temperate zone fruit and nut crops. In: Debergh, P. C. and Zimmerman, R. H. (eds.) Micropropagation: Technology and application. Kluwer, Dordreckt; El Shiekh, A.; Wildung, D. K.; Luby, J. J.; Sargent, K. L.; Read, P. E. "Long term effects of propagation by tissue culture or softwood single node cuttings on growth habit, yield, and berry weight of 'Northblue' blueberry," Journal of the American Society for Horticultural Science. 1996, 121: 2, 339 342; Galletta, G. J.; Ballington, J. R.; Daubeny, H. A.; Brennan, R. M.; Reisch, B. J.; Pratt, C.; Ferguson, A. R.; Seal, A. G.; McNeilage, M. A.; Fraser, L. G.; Harvey, C. F.; Beatson, R. A.; Hancock, J. F.; Scott, D. H.; Lawrence, F. J.; Janick, J. (ed.); Moore, J. N. "Fruit breeding. Volume II. Vine and small fruits," Department of Horticulture, Purdue University, West Lafayette, Ind. 1996 John Wiley and Sons; New York; USA; Strik, B.; Brun, C.; Ahmedullah, M.; Antonelli, A.; Askham, L.; Barney, D.; Bristow, P.; Fisher, G.; Hart, J.; Havens, D. Draper A D. and Chandler C. K. "Accelerating highbush blueberry selection evaluation by early propagation," Journal of the American Society for Horticultural Science. 1986 111 (2): 301-303; Pritts M. P. and Hancock J. F. (Eds.) "Highbush blueberry production guide," Northeast Regional Agricultural Engineering Service, Ithaca, N.Y., USA 1992.

The fruiting season of 'Osorno' significantly overlaps that of the widely planted, mid-season cultivars 'Draper,' and 'Bluecrop.' 'Osorno' has larger fruit than 'Bluecrop,' as well as more highly-rated overall fruit quality. It is a little larger than 'Draper' with comparable fruit quality, but a sweeter taste. It is a much more vigorous than 'Draper' and likely more productive. 'Osorno' is meant as a very heat tolerant alternative to 'Draper,' where the vigor of 'Draper' may be an issue.

'Osorno' is likely not as winter hardy as 'Bluecrop' and 'Draper.' It displayed consistent high yields in Michigan until 2011, when a sharp temperature reduction in early winter destroyed a high proportion of its flower buds. At Grand Junction, Mich., 'Osorno' lost about 70% of its flower buds, while 'Bluecrop' and 'Draper' lost about 40%. 'Osorno' flower buds were little damaged in the winter of 2011/2012, but this winter was unseasonably mild. No winter damage has been noted on 'Osorno' in Oregon or Chile.

'Osorno' is intended for all northern highbush production areas where winters are not severe, such as central Chile, Western Europe, and the Pacific Northwest (USDA Plant Hardiness Zone 6a). 'Osorno' has a chilling requirement of 800-1000 hours. It has high yields and vigor, as well as exceptional fruit quality, i.e., very large, light blue, tiny scar, extremely firm and crisp, and flavor that is balanced sweet. However, 'Osorno' may have only modest winter hardiness and a bush habit that can be difficult to mechanically harvest.

'Osorno' characteristics are set forth in Table 1, below. Taxonomic characteristics disclosed herein are standard in the practice (R E Gough, R J Hindle, and V G Shutak, "Identification of Ten Highbush Blueberry Cultivars using Morphological Characteristics," *HortScience* 11 (5): 512-4, 1976). Color descriptions, except those given in common terms, are presented in Royal Horticultural Society Colour Chart designations. In cases where the color descriptions cited from The Royal Horticultural Society Colour Chart differ from the colors shown in the drawings, the colors cited from The Royal Horticultural Society Colour Chart should be considered accurate. Any deviation from these colors in the drawings is due to failure of the photographic process to exactly duplicate the colors of nature. In addition, fruit color designations in Table 1 are applicable only to mature fruit.

TABLE 1

'Osorno' Characteristics

| Characteristic | 'Osorno' |
|---|---|
| Plant Traits | |
| Mature height | 1.4 m |
| Mature width | 1.1 m |
| Height/width ratio | 1.19 |
| Growth habit | Bushy, upright |
| Annual renewal canes | 3 to 5 |
| Internode length on spring shoots | 1-2 cm (1.36 cm average) |
| Mature cane color | grayed-green (198A) |
| Mature cane length | 0.80-1.20 m (0.95 m average) |
| Mature cane width | 1.0-1.5 cm (1.4 cm average) |
| Bark texture | smooth to moderately rough |
| Vigor | strong |
| Fall color on new shoots | yellowish green (145B) |
| One-year-old shoot color | green (144C) |
| One-year-old shoot: length of internode | 15-23 mm (18.2 mm average) |
| Fruiting type | on one-year-old shoots only |
| Time of vegetative bud burst | early to mid-May |
| Time of beginning of flowering on one-year-old shoot | late April to mid-May |
| Time of beginning of fruit ripening on one-year-old shoot | late July to early August |
| Foliage | |
| Leaf shape | elliptic |
| Apex shape | acute |
| Base shape | rounded |
| Leaf length | 4.2-5.0 cm (4.7 cm average); medium |
| Leaf width | 2.5-3.1 cm (2.8 cm average); medium |
| Leaf length/width ratio | 1.7; medium |
| Leaf margin | entire |
| Leaf nectaries | absent |
| Pubescence | none |

TABLE 1-continued

| 'Osorno' Characteristics | |
|---|---|
| Characteristic | 'Osorno' |
| Color upper surface | green (137C) |
| Intensity of green on upper surface | medium |
| Color lower surface | green (138B) |
| Petiole length | 1.4 cm (1-2 cm average) |
| Petiole diameter | 1.5-2.5 mm (2.0 average) |
| Petiole color | light yellowish green (142C) |
| Bud | |
| Bud shape | ovate |
| Bud width | 2.0-4.0 mm (3.2 mm average) |
| Bud length | 5.0-7.0 mm (5.4 mm average) |
| Color | grayed-green (197B) |
| Flower bud anthocyanin coloration | absent |
| Inflorescence length (excluding peduncle) | 4.2-5.2 cm (4.6 cm average) |
| Blossoms | |
| Shape of corolla | elongate-urceolate |
| Size of corolla tube: length | 10-11 mm (10.5 mm average) |
| Size of corolla tube: diameter | 5.0-6.0 mm (5.7 mm average) |
| Anthocyanin coloration of corolla tube | absent |
| Petals | 5 (fused) |
| Petal length | 10-11 mm (10.5 mm average) |
| Calyx | 5 lobed |
| Style length | 10-11 mm at corolla tip to slightly longer |
| Color of open flower | white |
| Flower # per cluster | 4-5 |
| Pistil | one per flower |
| Pistil color | yellowish green (145A) |
| Pistil length | 10-11 mm |
| Flower diameter | 7-8 mm |
| Flower length | 10-11 mm |
| Fragrance | faint blueberry aroma |
| Calyx diameter | 6 mm |
| Sepals | fused, 5 lobes |
| Color top | yellowish green (146C) |
| Color bottom | yellowish green (146C) |
| Unripe fruit: intensity of green color | medium |
| Reproductive organs | |
| Type | berry |
| Seed size | 1.75 mm |
| Number of seeds | 4-30 (9.1 average) |
| Mature fruit | |
| Size | large |
| Height | 1.5-1.6 cm (1.52 cm average) |
| Width | 1.7-2.2 cm (1.75 cm average) |
| Shape in longitudinal direction | round |
| Diameter of calyx basin | 6.0-7.5 mm (6.5 mm average) |
| Depth of calyx basin | 3.0-3.5 mm (3.3 mm average) |
| Color with bloom | violet blue (98B) |
| Color without bloom | violet blue (103A) |
| Color of skin after removal of bloom | violet blue (103A) |
| Intensity of bloom | strong |
| Firmness | very firm |
| Pedicel scar size | 2-3 mm (2.2 mm average) |
| Pedicel length | 8-10 mm (9 mm average) |
| Pedicel color | yellowish green (144B) with red (60B) blush |
| Peduncle length | 9-10 cm |
| Peduncle color | yellowish green (138A) |
| Average weight | 2.9 g |
| Sepals | none remaining on ripe fruit |
| Cluster density | medium |
| Sweetness | medium |
| Acidity | medium |

In multi-location trials, 'Osorno' has been a semi-spreading bush that ripens fruit in the early mid-season, as illustrated in Table 2, below. Specifically, development and fruit characteristics of 'Osorno' were evaluated at two locations in Michigan, two in Oregon, and one in Chile. Two year old plants were set at 4×10 foot spacing in 2008 in Michigan, and 2009 in Oregon and Chile. Evaluations were made when the bushes were 30-50% ripe. Its fruit have had excellent size, color, firmness and flavor. It also has had high vigor and excellent yields, except in Michigan in 2011 (after the severe winter).

TABLE 2

Development and Fruit Characteristics
For bush habit: 1 = sprawling, 5 = bushy, and 9 = upright.
For season: 1 = very early, 4-5 = midseason, and 9 = very late.
For vigor and fruit characteristics: 1-4 = inferior, 5-6 = acceptable, 7 = good, 8 = excellent, and 9 = superior.

| | | | Fruit Characteristics | | | | |
|---|---|---|---|---|---|---|---|
| Location | City | Year | Habit | Season | Vigor | Yield | Size |
| Michigan | Grand Junction | 2010 | 7 | 4 | 7 | 7 | 8 |
| | | 2011 | 6 | 4 | 6 | 2 | 8 |
| | | 2012 | 7 | 4 | 5 | 7 | 9 |
| | South Haven | 2010 | 4 | 5 | 7 | 8 | 7 |
| | | 2011 | 6 | 5 | 8 | 2 | 8 |
| | | 2012 | 7 | 4 | 8 | 9 | 7 |
| | | Mean | 6.2 | 4.3 | 6.8 | 5.8 | 7.8 |
| Oregon | Lowell | 2010 | 6 | 5 | — | 6. | 8 |
| | | 2011 | 4 | 4 | 9 | 9 | 7 |
| | Silverton | 2010 | 5 | 4 | — | 7 | 9 |
| | | 2011 | 4 | 4 | 7 | 7 | 8 |
| | | Mean | 4.8 | 4.3 | 8.0 | 7.3 | 8.0 |
| Chile | Osorno | 2010 | 4 | 5 | 7 | 7 | 6 |
| | | 2011 | 6 | 4 | 8 | 7 | 8 |
| | | Mean | 5.0 | 4.5 | 7.5 | 7.0 | 7.0 |
| | Grand Mean | | 5.3 | 4.4 | 7.4 | 6.7 | 7.6 |

| | | | Fruit Characteristics | | | |
|---|---|---|---|---|---|---|
| Location | City | Year | Color | Scar | Firmness | Flavor |
| Michigan | Grand Junction | 2010 | 7 | 9 | 8 | 8 |
| | | 2011 | 8 | 8 | 8 | 8 |
| | | 2012 | 9 | 8 | 8 | 7 |
| | South Haven | 2010 | 7 | 8 | 8 | 8 |
| | | 2011 | 8 | 8 | 8 | 8 |
| | | 2012 | 8 | 9 | 8 | 8 |
| | | Mean | 7.8 | 8.3 | 8.0 | 7.8 |
| Oregon | Lowell | 2010 | 8 | 8 | 8 | 7 |
| | | 2011 | 8 | 8 | 9 | 7 |
| | Silverton | 2010 | 6 | 9 | 7 | 7 |
| | | 2011 | 7 | 8 | 8 | 8 |
| | | Mean | 7.3 | 8.3 | 8.0 | 7.3 |
| Chile | Osorno | 2010 | 6 | 7 | 8 | 7 |
| | | 2011 | 9 | 8 | 9 | 9 |
| | | Mean | 7.5 | 7.5 | 8.5 | 8.0 |
| | Grand Mean | | 7.5 | 8.0 | 8.2 | 7.7 |

In comparative Michigan trials, 'Osorno' has ripened at about the same time as 'Draper' and 'Bluecrop,' as illustrated in Table 3, below. Specifically, mean fruit rating and ranges of 'Osorno,' 'Draper,' and 'Bluecrop' were evaluated at Grand Junction and South Haven, Mich. in 2010, 2011, and 2012. Two year old plants were set in 2008. Fruit evaluations were made when the bushes were 50% ripe. 'Osorno' has rated higher than 'Bluecrop' in all measured characteristics. The fruit of 'Osorno' have been larger and received higher flavor scores than 'Draper' with a comparable scar, although the fruit of 'Osorno' have been a little darker.

TABLE 3

Mean Fruit Rating and Ranges
The rating scale is 1-9, with 1-4 = inferior, 5-6 = acceptable, 7 = good, 8 = excellent, and 9 = superior.
Ranges are in parentheses.

| Cultivar | Date Full bloom | Date 50% ripe | Plant vigor[1] | Weight | Color |
|---|---|---|---|---|---|
| 'Osorno' | 5/9 (4/26-5/16) | 7/1 (6/29-7/3) | 7.5 (5-8) | 7.8 (7-9) | 7.8 (7-8) |
| 'Draper' | 5/11 (4/23-5/20) | 7/3 (6/27-7/7) | 6.5 (6-7) | 7.6 (7-9) | 8.5 (8-9) |
| 'Bluecrop' | 5/11 (4/23-5/20) | 7/5 (6/29-7/21) | 6.9 (6-7) | 6.5 (6-7) | 7.5 (7-8) |

| Cultivar | Picking scar | Firmness | Flavor | Fruit load[2] |
|---|---|---|---|---|
| 'Osorno' | 8.3 (8-9) | 8.0 (all 8s) | 7.8 (7-9) | 5.6 (2-8) |
| 'Draper' | 8.6 (8-9) | 8.8 (8-9) | 7.2 (7-8) | 6.5 (5-9) |
| 'Bluecrop' | 7.2 (7-8) | 7.3 (7-8) | 6.5 (5-7) | 7.2 (5-9) |

[1]A block of 'Osorno' at Grand Junction is at the edge of the field and is doing poorly (rating of 5). Osorno at all other locations is very vigorous (ratings 7-9).
[2]A sharp temperature reduction in the winter of 2011 damaged a high proportion of the flower buds of most cultivars. 'Osorno' lost about 70%, while young plants of 'Bluecrop' and 'Draper' lost about 40%. 'Osorno', 'Draper' and 'Bluecrop' had comparable winter damage in the other years.

As illustrated in Table 4, below, the fruit weight of 'Osorno' has been larger than the standard cultivars in most comparisons in Michigan, except it was smaller than 'Legacy' in Chile. Specifically, average fruit physical and biochemical characteristics of 'Osorno' were compared to standard cultivars in Osorno, Chile (2012) and Grand Junction, Mich. (2011 and 2012). Five-fruit samples were evaluated when the bushes were 30-50% ripe. Soluble solids in the fruit of 'Osorno' have been comparable to all the standard cultivars except 'Liberty' and its titratable acidity has been among the lowest of any cultivar. Its fruit have also been very firm, comparable to 'Draper' and 'Liberty' in Michigan and superior to 'Liberty' in Chile.

TABLE 4

Average Fruit Characteristics

| Cultivar | Location | Year | Weight (g) | Soluble solids | Titratable acidity |
|---|---|---|---|---|---|
| Osorno | Michigan | 2011 | 2.9 | 12.5 | 0.81 |
| | | 2012 | 1.9 | 13.0 | 0.53 |
| | Chile | 2012 | 1.9 | 15.9 | 0.66 |
| Draper | Michigan | 2011 | 2.1 | 12.7 | 0.89 |
| | | 2012 | 1.7 | 11.9 | 1.05 |
| Bluecrop | Michigan | 2011 | 1.6 | 11.1 | 0.80 |
| | | 2012 | 1.6 | 11.8 | 0.67 |
| Legacy | Michigan | 2011 | 2.0 | 12.1 | 0.73 |
| | | 2012 | 2.1 | 13.3 | 0.52 |
| | Chile | 2012 | 2.2 | 13.8 | 0.40 |

TABLE 4-continued

Average Fruit Characteristics

| | | | | | |
|---|---|---|---|---|---|
| Liberty | Michigan | 2011 | 1.8 | 15.4 | 0.85 |
| | | 2012 | 1.7 | 15.8 | 0.53 |
| | Chile | 2012 | 2.4 | 14.8 | 0.70 |
| Jersey | Michigan | 2011 | 1.4 | 13.2 | 0.51 |
| | | 2012 | 1.2 | 13.8 | 0.63 |

| Cultivar | Location | Year | SS/TA | Firmness (g/mm) | Firmness (N) |
|---|---|---|---|---|---|
| Osorno | Michigan | 2011 | 15.4 | — | — |
| | | 2012 | 24.2 | 332 | — |
| | Chile | 2012 | 24.0 | — | 51.7 |
| Draper | Michigan | 2011 | 14.3 | — | — |
| | | 2012 | 12.1 | 334 | — |
| Bluecrop | Michigan | 2011 | 13.9 | — | — |
| | | 2012 | 17.6 | 202 | — |
| Legacy | Michigan | 2011 | 16.6 | — | — |
| | | 2012 | 25.6 | 301 | — |
| | Chile | 2012 | 34.5 | — | 37.6 |
| Liberty | Michigan | 2011 | 18.2 | — | |
| | | 2012 | 29.8 | 322 | |
| | Chile | 2012 | 21.1 | | 43.1 |
| Jersey | Michigan | 2011 | 25.9 | — | — |
| | | 2012 | 21.9 | 202 | — |

As illustrated in Table 5, the fruit of 'Osorno' have a larger size, smaller picking scar, and are more firm than the fruit of 'Bluecrop.' Relative to the vigor of 'Draper,' the vigor of 'Osorno' is high.

TABLE 5

Expression Characteristics

| Cultivar | Characteristic | Expression of the characteristic in the cultivar | Expression of the characteristic in 'Osorno' |
|---|---|---|---|
| 'Bluecrop' | fruit size | medium to large | very large |
| 'Bluecrop' | picking scar | medium to small | very small |
| 'Bluecrop' | firmness | medium to firm | very firm |
| 'Draper' | plant vigor | low to medium | medium to high |

'Osorno' is distinct from its female parent 'Draper' in that 'Osorno' plants have: slightly larger fruit; sweeter fruit; stronger vigor; higher productivity; and lower winter hardiness. 'Osorno' is similar to 'Draper' in that their seasons can overlap.

'Osorno' is distinct from its male parent 'Legacy' in that 'Osorno' plants produce firmer, lighter colored fruit but are less vigorous. 'Osorno is similar to 'Legacy' in that they have about the same winter hardiness.

What is claimed is:

1. A new and distinct highbush blueberry plant, substantially as illustrated and described herein.

* * * * *